United States Patent
Douglas et al.

(10) Patent No.: US 9,725,387 B2
(45) Date of Patent: *Aug. 8, 2017

(54) TREATMENT OF ALCOHOLS

(71) Applicant: TECHNIP E&C LIMITED, Buckinghamshire (GB)

(72) Inventors: Thomas Mark Douglas, East Yorkshire (GB); Andrew John Hogben, East Yorkshire (GB); David John Law, East Yorkshire (GB); John Glenn Sunley, East Yorkshire (GB); Thomas Giles Parsons, Middlesex (GB)

(73) Assignee: TECHNIP E&C LIMITED, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/428,067

(22) PCT Filed: Sep. 12, 2013

(86) PCT No.: PCT/EP2013/068948
§ 371 (c)(1),
(2) Date: Mar. 13, 2015

(87) PCT Pub. No.: WO2014/041094
PCT Pub. Date: Mar. 20, 2014

(65) Prior Publication Data
US 2015/0232399 A1 Aug. 20, 2015

(30) Foreign Application Priority Data
Sep. 12, 2013 (EP) .................................. 12184420

(51) Int. Cl.
*C07C 29/76* (2006.01)
*C07C 1/24* (2006.01)

(52) U.S. Cl.
CPC .............. *C07C 29/76* (2013.01); *C07C 1/24* (2013.01); *C07C 2529/06* (2013.01); *C07C 2529/85* (2013.01)

(58) Field of Classification Search
CPC .................................. C07C 29/76; C07C 1/24
USPC ........................................................ 568/917
See application file for complete search history.

(56) References Cited

U.S. PATENT DOCUMENTS

2011/0009677 A1   1/2011   Kikuchi et al.

FOREIGN PATENT DOCUMENTS

| WO | WO 2007/025472 A1 | 3/2007 | |
|---|---|---|---|
| WO | WO 2010/060981 A1 | 6/2010 | |
| WO | WO 2010060981 A1 * | 6/2010 | ............... C07C 1/24 |

* cited by examiner

Primary Examiner — Sudhakar Katakam
Assistant Examiner — Kofi Adzamli
(74) Attorney, Agent, or Firm — Nixon & Vanderhye P.C.

(57) ABSTRACT

Process for treating an alcohol composition containing nitrogen-containing contaminants by contacting the alcohol composition with an adsorbent in an adsorption zone. The adsorbent is a transition metal-loaded solid porous material selected from aluminosilicates, silica-aluminas, silicates and aluminas, and the alcohol composition is contacted with the adsorbent either alone or in the presence of an inert carrier gas.

19 Claims, 10 Drawing Sheets

TREATMENT OF ALCOHOLS

This application is the U.S. national phase of International Application No. PCT/EP2013/068948 filed Sep. 12, 2013 which designated the U.S. and claims priority to European Patent Application No. 12184420.3 filed Sep. 14, 2012, the entire contents of each of which are hereby incorporated by reference.

This invention provides a process for the treatment of alcohol compositions to remove nitrogen-containing contaminants. Also provided is a process for the preparation of olefins from alcohols by dehydration, the process comprising treating an alcohol composition to remove nitrogen-containing contaminants prior to dehydration of the alcohols. Also provided are alcohol compositions obtainable by the treatment process of the present invention.

BACKGROUND OF THE INVENTION

Alcohols, such as saturated monohydric alcohols, are important chemical commodities which may be used as fuels or as components of fuels, as solvents, and as feedstocks for the preparation of other important commodity chemicals. Ethanol in particular is widely used commercially as a gasoline additive or as a fuel per se, as a solvent, as a germicide, as an antifreeze, as a component in the food and beverage industry, and as a chemical feedstock.

Ethanol, and to a lesser extent propanol and butanol, are of increasing significance as chemical feedstocks, since they are readily obtainable from biological sources, in particular by the fermentation of sugars and/or biomass. Alcohols from biological sources, so-called bio-alcohols, thus provide one way of reducing the dependence on crude oils for fuel uses and as chemical feedstocks.

Bio-alcohols, and bio-ethanol in particular, are typically produced by fermentation processes performed on biomass and/or derivatives thereof. As used herein, the term "biomass" includes sugar sources, for instance sugar beet, sugar cane, molasses and corn syrup, starches and cellulosic materials, such as lignocellulose. Starches and cellulosic materials are generally converted by enzymatic or chemical hydrolysis to produce simple sugars which can then be converted to bio-alcohols by fermentation. Ethanol obtained from cellulosic materials is commonly referred to as cellulosic ethanol or lignocellulosic ethanol.

Alcohols obtained by fermentation contain low levels of nitrogen-containing contaminants. One possible source of nitrogen-containing contaminants may be ammonia which may be introduced during the fermentation stage. Once in the process, the ammonia can react with ethanol and other impurities to form a variety of nitrogen-containing compounds. Nitrogen-containing contaminants are also often present in alcohols from other sources.

The presence of nitrogen-containing contaminants in alcohol compositions is undesirable since these compounds may interfere with subsequent chemical processing in which the alcohol composition is used as a feedstock. For example, nitrogen-containing contaminants can poison, deactivate or otherwise interfere with a number of catalysts which may be used in the processing of alcohol feedstocks, for example by neutralising acidic sites on heterogeneous acidic catalysts.

An example of the use of heterogeneous acidic catalysts for the processing of alcohols is the dehydration of alcohols to form olefins. Olefins, such as ethylene, have historically been produced by steam or catalytic cracking of hydrocarbons derived from crude oil. However, as crude oil is a finite resource, methods for the preparation of olefins by the dehydration of alcohols have been proposed. For instance, WO 2009/098262 discloses a process for the catalytic dehydration of an alcohol to the corresponding olefin wherein the catalyst is selected from a crystalline silicate, a dealuminated crystalline silicate or a phosphorus modified zeolite; WO 2008/138775 discloses a process for the dehydration of one or more alcohols comprising contacting one or more alcohols with a supported heteropolyacid catalyst in the presence of one or more ethers; and WO 2008/062157 discloses a heteropolyacid catalyst and the use thereof in a process for the production of olefins from oxygenates.

Olefins produced in this way have a range of potential applications, for instance as feedstocks for the production of polymeric materials. In particular, ethylene obtained by the dehydration of ethanol may usefully be processed into polyethylene. Similarly, the dehydration of propanols provides a route to propylene which may subsequently be processed into polypropylene.

It has been observed that catalysts used for the dehydration of alcohols, such as crystalline silicate, dealuminated crystalline silicate, phosphorus modified zeolite or supported heteropolyacid catalysts, are sensitive to the presence of low levels of nitrogen-containing contaminants in alcohol feedstocks. Consequently, in order to ensure commercially acceptable catalyst performance and lifetime, it is highly desirable to treat alcohol feedstocks to remove the nitrogen-containing contaminants prior to the dehydration reaction. As noted above, the presence of low levels of nitrogen-containing contaminants is a feature of alcohol compositions obtained from at least biological sources.

The use of cation exchange resins and sorbents for the removal of nitrogen-containing compounds from hydrocarbon streams is known in the petrochemical industry. However, the sensitivity of many acidic catalysts, such as the supported heteropolyacid catalysts mentioned above, to nitrogen-containing contaminants is such that very stringent removal of these compounds is required, for instance to 1 ppm or less, preferably 0.5 ppm or less, and most preferably 0.2 ppm or less; very low concentrations of nitrogen-containing contaminants are desirable in order to obtain a useful catalyst lifetime. It has been observed that the use of cation exchange resins alone may be inadequate to obtain such stringent removal of nitrogen-containing contaminants from alcohol compositions and that additional treatment of the alcohol composition may be required. It is therefore of significant commercial interest to be able to identify new processes which are able to remove nitrogen-containing contaminants from alcohols, particularly bio-alcohols such as bio-ethanol.

WO 1997045392 discloses a process for the production of ethers in which deactivation of an acidic ion-exchange resin etherification catalyst is reduced by separating nitriles from an olefin feedstock by aqueous extraction. The nitriles are subsequently separated into an alcohol phase and hydrogenated to form amines which are more easily separable from the alcohol phase by fractionation.

EP 1 176 132 A1 discloses a process for preparing ethers comprising reacting an alcohol and an olefin in the presence of an acidic catalyst. Excess alcohol is recycled to the reaction zone together with nitrile compounds originating from the olefin feed. To avoid accumulation of nitriles in the system and deactivation of the catalyst, the excess alcohol comprising nitrile compounds is contacted in the liquid phase with a solid acid prior to being recycled to the reaction zone. It is reported that this reduces the level of nitriles in the recycled alcohol stream by at least 50%.

U.S. Pat. No. 6,770,790 discloses a process for removing oxygen-containing impurities from tertiary butyl alcohol comprising contacting the tertiary butyl alcohol in the liquid phase with at least two solid adsorbents, wherein the at least two solid adsorbents comprise aluminium oxide and a large pore zeolite.

WO 2010/060981 discloses a process for the purification of an alcohol in the course of a process for the preparation of olefins by acid-catalysed dehydration of the alcohol, the process comprising contacting the alcohol with one or more adsorbent materials. It is disclosed in WO 2010/060981 that while ammonia and amines can be adsorbed, nitrile impurities such as acetonitriles must be hydrogenated to provide modified impurities which are more readily adsorbed. Thus, according to WO 2010/060981, the alcohol is subjected to a hydrogenation step prior to contacting the alcohol with the one or more adsorbent materials. The Examples of WO 2010/060981 teach the removal of basic compounds from bio-ethanol by adsorption on a sulfonic acid resin at ambient temperature and pressure.

SUMMARY OF THE INVENTION

There remains a need in the art for processes which are able to remove substantially completely nitrogen-containing contaminants from alcohols, particularly bio-alcohols such as bio-ethanol. Preferably such a process would provide a further reduction in the residual content of nitrogen-containing compounds of the treated alcohol over what has been reported in the art to date. Still more preferably, such a process would avoid the need for pre-treatment of the alcohols (e.g. by hydrogenation) to convert nitrogen-containing contaminants, such as nitriles, into modified contaminants that are more easily removed.

In a first aspect, the present invention provides a process for the treatment of an alcohol composition comprising nitrogen-containing contaminants, the process comprising contacting the alcohol composition with an adsorbent in an adsorption zone, wherein the adsorbent is a transition metal-loaded solid porous material selected from the group consisting of aluminosilicates, silica-aluminas, silicates and aluminas, preferably the adsorbent is a transition metal-loaded solid porous material selected from the group consisting of aluminosilicates and silica-aluminas.

Following contact with the adsorbent, a treated alcohol composition may be recovered which has a reduced content of nitrogen-containing contaminants compared with the untreated alcohol composition. This treated alcohol composition is suitable for use in a number of chemical processes, and in particular those types of chemical processes which are sensitive to the presence of nitrogen-containing contaminants in alcohol feedstocks.

Thus, in another aspect (also referred to herein as the 'second aspect' of the present invention), the present invention provides a process for the preparation of olefins from an alcohol composition comprising a dehydratable alcohol and nitrogen-containing contaminants, the process comprising:

(i) contacting the alcohol composition with an adsorbent in an adsorption zone, wherein the adsorbent is a transition metal-loaded solid porous material selected from the group consisting of aluminosilicates, silica-aluminas, silicates and aluminas, preferably the adsorbent is a transition metal-loaded solid porous material selected from the group consisting of aluminosilicates and silica-aluminas, to form a treated alcohol composition; and (ii) contacting the treated alcohol composition with an alcohol dehydration catalyst in an alcohol dehydration zone under conditions effective to dehydrate the alcohol to the corresponding olefin.

In a further aspect, the present invention provides an alcohol composition derived from the fermentation of biomass and/or biomass derivatives and having a total nitrogen concentration of 0.25 ppmw (parts per million by weight) or less, such as 0.1 ppmw or less or 0.05 ppmw or less. Such an alcohol composition is obtainable by the process according to the first aspect of the invention.

In a further aspect, the present invention provides an alcohol composition derived from the fermentation of biomass and/or a derivative thereof, and having a content of nitrogen in the form of nitriles below 0.1 ppmw, preferably below 0.05 ppmw, more preferably below 0.04 ppmw, such as below 0.03 ppmw or even below 0.02 ppmw. Such an alcohol composition is obtainable by the process according to the first aspect of the invention.

In a further aspect, the present invention provides the use of a transition metal-loaded solid porous material selected from the group consisting of aluminosilicates, silica-aluminas, silicates and aluminas, as an adsorbent in the removal of nitrogen-containing contaminants, in particular nitrile compounds, from an alcohol composition containing said nitrogen-containing contaminants by contacting said alcohol composition with said transition metal-loaded solid porous material selected from the group consisting of aluminosilicates, silica-aluminas, silicates and aluminas. Preferably the transition metal-loaded solid porous material selected from the group consisting of aluminosilicates, silica-aluminas, silicates and aluminas is a transition metal-loaded solid porous material selected from the group consisting of aluminosilicates and silica-aluminas.

The present inventors have found that by loading a solid porous material selected from the group consisting of aluminosilicates, silica-aluminas, silicates and aluminas with a transition metal, the process of the present invention is unexpectedly more effective for the removal of nitriles than a corresponding process that uses a solid porous material selected from the group consisting of aluminosilicates, silica-aluminas, silicates and aluminas which is not loaded with a transition metal. Therefore, the process of the present invention can remove or reduce the concentration of nitriles in an alcohol composition without the necessity to first subject the alcohol composition to a hydrogenation step.

The present inventors have also found that the removal of nitrogen-containing contaminants from alcohols is enhanced if the alcohol composition is in the vapour phase when it is contacted with the adsorbent, whereas it would be expected that the higher temperatures and/or reduced pressures required would promote desorption of the nitrogen-containing contaminants from the adsorbent.

As used herein, the term "alcohol composition" refers to a composition which comprises at least 50 wt % alcohol. Preferably, an alcohol composition to be treated according to the process of the present invention comprises at least 90 wt % alcohol, more preferably at least 95 wt % alcohol, such as at least 98 wt % alcohol or at least 99 wt % alcohol.

The alcohol composition may additionally comprise an inert component, wherein said inert component is any component which does not react with alcohols or adversely affect the alcohol treatment step under the conditions used and would not adversely affect a process for the dehydration of alcohols. By way of example, the inert component may be selected from saturated hydrocarbon compounds having from 1 to 10 carbon atoms, naphthenes, water and inert gases such as nitrogen. Advantageously, the alcohol composition may comprise water. For example, the alcohol composition may be a hydrous alcohol composition which has not been subjected to a dewatering step.

The alcohol composition may comprise a single type of alcohol, or it may comprise a mixture of two or more different alcohols. In one particular embodiment the alcohols present in the alcohol composition are substantially a single type of alcohol, that is, at least 95 wt % of the alcoholls present in the alcohol composition are alcohols having the same number of carbon atoms, preferably at least 98 wt %, such as at least 99 wt % or at least 99.5 wt %, of the alcohols present in the alcohol composition are alcohols having the same number of carbon atoms. In this embodiment, it is preferably that the alcohols having the same carbon number also are substantially of a single isomeric form of the alcohols having the same carbon number.

The alcohol composition preferably comprises one or more alcohols selected from $C_1$ to $C_6$ saturated monohydric alcohols, more preferably $C_2$ to $C_6$ saturated monohydric alcohols, and still more preferably $C_2$ to $C_4$ saturated monohydric alcohols.

Preferably, the one or more alcohols are selected from dehydratable $C_2$ to $C_6$ saturated monohydric alcohols, and more preferably from dehydratable $C_2$ to $C_4$ saturated monohydric alcohols. By dehydrateable alcohol, it is meant that the alcohol is capable of being converted into the corresponding olefin through the loss of a water molecule.

In one particular embodiment, the alcohol composition comprises one or more alcohols selected from ethanol, 1-propanol, 2-propanol, 1-butanol, 2-butanol and isobutanol (2-methyl-propan-1-ol), more preferably an alcohol selected from ethanol, 1-propanol and isobutanol, and most preferably the alcohol composition comprises ethanol.

In one particular embodiment, the alcohol composition comprises one or more alcohols produced from a biological source, for example by fermentation of biomass and/or a derivative thereof. The term "biomass" as used herein refers to any biological source of a carbohydrate which may be converted to an alcohol by fermentation of the biomass directly or fermentation of a derivative of the biomass; for example biological sources of sugars, starches and cellulose. For instance, bio-alcohols, such as bio-ethanol, may be obtained by the fermentation of sugars from sources such as sugar beet, sugar cane, molasses or corn syrup. Examples of alcohols produced from biological sources include bio-ethanol, bio-propanol and bio-butanol. In one particular embodiment, the alcohol composition comprises bio-ethanol, such as obtained by fermentation of feedstocks derived from sugar cane, such as sugar cane molasses and sugar cane juice; sugar beet, such as sugar beet molasses and sugar beet juice; cereal crops, such as corn or wheat derived feedstocks like corn syrup; and lignocellulosic materials, such as fast growing grasses or "energy grasses".

In one particular embodiment, the alcohol composition comprises at least 50 wt % ethanol, preferably at least 90 wt % ethanol, more preferably at least 95 wt % ethanol, such as at least 98 wt % ethanol or at least 99 wt % ethanol. In one aspect of this embodiment, the ethanol is bio-ethanol.

In one embodiment of the present invention, the alcohol composition is a hydrous ethanol composition. Such hydrous ethanol compositions may be the raw or crude ethanol composition which is the resultant from the distillation of an ethanol product which has been obtained by the fermentation of biomass without further subjecting the obtained ethanol to a dewatering step. Such hydrous ethanol compositions may contain an amount of water which is equal to or greater than the amount of water which is determined by the azeotrope of the ethanol water composition produced during the fermentation process.

The concentration of nitrogen-containing contaminants in the alcohol composition to be treated according to the process of the present invention will generally be at a level which is detrimental to the performance of an acidic alcohol dehydration catalyst, such as a supported heteropolyacid catalyst. In this disclosure, the concentration of nitrogen-containing contaminants is reported as parts per million by weight (ppmw) of the total nitrogen content of said nitrogen-containing contaminants. References herein to ppmw of nitrogen shall be interpreted as ppmw of nitrogen in the form of nitrogen-containing contaminants.

Thus, the alcohol composition to be treated according to the process of the invention preferably comprises at least 0.2 ppmw (parts per million by weight) of nitrogen, more preferably at least 0.25 ppmw of nitrogen, more preferably at least 0.3 ppmw of nitrogen, still more preferably at least 0.4 ppmw of nitrogen, and most preferably at least 0.5 ppmw of nitrogen. For instance, the alcohol composition to be treated according to the process of the invention may comprise at least 0.6 ppmw, at least 0.7 ppmw, at least 0.8 ppmw, at least 0.9 ppmw or at least 1.0 ppmw of nitrogen.

The upper limit of the nitrogen concentration of the alcohol composition is not critical to the invention. Thus, concentrations of nitrogen-containing contaminants of over 100 ppmw of nitrogen, such as over 200 ppmw of nitrogen, over 500 ppmw of nitrogen, or even over 1000 ppmw of nitrogen, are readily treatable by the process of the present invention. However, to avoid rapid exhaustion of the adsorbent it may be preferable that the alcohol composition comprises 50 ppmw or less of nitrogen, more preferably 25 ppmw or less of nitrogen, more preferably 10 ppmw or less of nitrogen, more preferably 8 ppmw or less of nitrogen, for instance 6 ppmw or less of nitrogen, 4 ppmw or less of nitrogen, or 2 ppmw or less of nitrogen. Thus, depending upon the initial concentration of nitrogen in the alcohol composition to be treated, it may be desirable to subject alcohol compositions comprising very high levels of nitrogen-containing contaminants to a pre-treatment step to reduce the level of nitrogen-containing contaminants. Such a pre-treatment may be carried out by any suitable technique, for instance by contacting the alcohol composition with an adsorbent in the liquid phase, such as an adsorbent may be an adsorbent as listed herein for use in the vapour phase or an acidic ion exchange resin.

As noted above, the process of the present invention can enable nitrile compounds to be substantially removed from an alcohol composition or for the concentration to be significantly reduced. Thus, in a preferred embodiment the alcohol composition to be treated according to the process of the invention comprises at least 0.025 ppmw nitrogen in the form of nitriles, more preferably at least 0.05 ppmw nitrogen in the form of nitriles, more preferably at least 0.10 ppmw nitrogen in the form of nitriles, such as at least 0.15 ppmw nitrogen in the form of nitriles, for instance at least 0.20 ppmw nitrogen in the form of nitriles, or even at least 0.25 ppmw nitrogen in the form of nitriles.

Where the alcohol composition is an ethanol-containing composition, at least a portion of the nitriles will be in the form of acetonitrile. Thus, in a further preferred embodiment, the alcohol composition is an ethanol-containing composition that comprises 0.05 ppmw nitrogen in the form of acetonitrile, preferably at least 0.10 ppmw nitrogen in the form of acetonitrile, such as at least 0.15 ppmw nitrogen in the form of acetonitrile, for instance at least 0.20 ppmw nitrogen in the form of acetonitrile, or even at least 0.25 ppmw nitrogen in the form of acetonitrile.

The concentration of nitrogen-containing contaminants in the alcohol composition to be treated according to the process of the invention may be determined by any suitable analytical technique known to persons of skill in the art. Suitable techniques include gas chromatography in conjunction with a nitrogen/phosphorus detector (GC-NPD), chemiluminescence methods and ion exchange chromatography. It has been found that GC-NPD is a particularly effective technique for observing individual nitrogen-containing species in the alcohol composition. The use of a nitrogen/phosphorus detector provides significantly enhanced signal strength for nitrogen compounds in comparison to carbon species (approximately $10^4$ enhancement). As a result, nitrogen compounds are clearly visible in the GC chromatogram along with the signals for the alcohol and in some cases the corresponding dialkyl ether.

A suitable chemiluminescence technique may involve vaporising and oxidizing an alcohol composition, measuring the concentration of nitrogen oxides in the vaporized and oxidized alcohol composition by chemiluminescence and hence determining the concentration of nitrogen atoms in the alcohol composition from the measured concentration of nitrogen oxides. Such techniques are described in further detail in U.S. Pat. No. 4,018,562 and GB 2373856.

The nitrogen-containing contaminants may include a number of different types of nitrogen-containing compounds, for instance nitriles (i.e. compounds containing one or more nitrile moiety, such as acetonitrile), amines (i.e. compounds containing one or more amine moiety, such as ammonia, methylamine, ethylamine, dimethylamine, diethylamine, triethylamine, trimethylamine, ethanolamine), ammonium cations, amides, imides and mixtures thereof; additionally, more complex and heterocyclic nitrogen-containing compounds, such as azines, diazines, pyrroles, diazoles, triazoles and tetrazoles and mixtures thereof, and more complex molecules containing one or more different nitrogen-containing moieties and optional other functional groups, such as amino acids, may also be present in the alcohol composition. Nitriles have low basicity due to the sp hybridization of the nitrogen atom which places the electron density of the nitrogen lone-pair close to the nitrogen nucleus, thus making the lone-pair relatively unreactive. Consequently, nitriles in particular pass through strong acid ion exchange resins with substantially no adsorption. Nonetheless, nitriles are found to be capable of quantitatively deactivating acidic catalysts used for alcohol dehydration processes. It has previously been proposed to carry out a pretreatment step to convert nitriles to amines by hydrogenation, as amines are more readily adsorbed. By employing the process of the present invention, a reduction in the concentration of all nitrogen-containing compounds to very low levels without the need to pretreat the alcohol composition to modify nitrile contaminants is achievable.

In preferred embodiments of the invention, the treated alcohol composition has a nitrogen content of less than 2 ppmw, more preferably less than 1 ppmw, still more preferably less than 0.5 ppmw, still more preferably less than 0.25 ppmw, such as less than 0.1 ppmw or less than 0.05 ppmw (50 parts per billion by weight, ppbw).

Where the alcohol composition to be treated according to the process of the invention contains nitriles, the treated alcohol composition preferably has a content of nitrogen in the form of nitriles below 0.1 ppmw, preferably below 0.05 ppmw, more preferably below 0.04 ppmw, such as below 0.03 ppmw or even below 0.02 ppmw. In a specific embodiment of the present invention, the treated alcohol composition is an alcohol composition derived from the fermentation of biomass and/or a derivative thereof, in particularly the alcohol composition is a bio-ethanol composition, and has a content of nitrogen in the form of nitriles below 0.1 ppmw, preferably below 0.05 ppmw, more preferably below 0.04 ppmw, such as below 0.03 ppmw or even below 0.02 ppmw.

The adsorbent used in the process of the present invention is a transition metal-loaded solid porous material selected from the group consisting of aluminosilicates, silica-aluminas, silicates and aluminas. Preferably, the adsorbent used in the process of the present invention is a transition metal-loaded solid porous material selected from the group consisting of aluminosilicates and silica-aluminas. Most preferably, the adsorbent used in the process of the present invention is a transition metal-loaded aluminosilicate. Preferred aluminosilicates for use in the adsorbent in the present invention are microporous and mesoporous aluminosilicates; especially preferred aluminosilicates are zeolites.

It is preferred that the adsorbent used in the process of the present invention contains acid sites or has an acid functionality. Therefore, the solid porous material selected from the group consisting of aluminosilicates and silica-aluminas of the adsorbent is preferably in the acidic form; in this regard, it is meant that the solid porous material selected from the group consisting of aluminosilicates and silica-aluminas of the adsorbent is in the acidic form prior to being loaded with the transition metal or is treated after the loading of the transition metal such that any sites which are not loaded with a transition metal ion are converted into the acidic form. Preferably, the solid porous material is in the acid form prior to the transition metal being loaded thereon.

The transition metal which is loaded on to the solid porous material in the adsorbent of the present invention is preferably selected from Groups 6, 7, 8, 9, 10, 11 and 12 of the Periodic Table; more preferably it is selected from zinc, copper, nickel, cobalt, iron, manganese, chromium, cadmium, silver, palladium, rhodium, ruthenium, molybdenum, mercury, gold, platinum, iridium, osmium, rhenium and tungsten; even more preferably it is selected from zinc, copper, nickel, cobalt, iron, manganese, chromium and silver. Copper has been found to be a particularly effective transition metal for use in the adsorbent of the present invention.

As used herein, the term "transition metal-loaded solid porous material selected from the group consisting of aluminosilicates, silica-aluminas, silicates and aluminas", and the like, refers a solid porous material selected from the specified list which has a transition metal supported or otherwise incorporated thereon. The transition metal may be loaded on to the solid porous material by any suitable means known in the art. Suitably, the transition metal may be loaded on to the solid porous material by means of impregnation or by ion-exchange of cation-exchangeable sites on the solid porous material where such sites area available thereon. Alternatively, the transition metal may be loaded by means of co-precipitation or co-mulling techniques.

If the transition metal is ion-exchanged on to the solid porous material, it is preferred that up to 80% of the cation-exchangeable sites present on the solid porous material may be bound to a transition metal ion, more preferably the amount of cation-exchangeable sites present on the solid porous material which are bound to a transition metal ion is in the range of from 1 to 50%, even more preferably from 2 to 40%, even more preferably from 3 to 30%, and most preferably from 5 to 25%, such as from 10 to 20%. Any sites that are not occupied by a transition metal cation are preferably occupied by a proton. Higher amounts of transition metal may be ion-exchanged, however, if higher amounts are used then it is preferred that the adsorbent is treated to provide some acid sites or acid functionality on the adsorbent.

If the transition metal is impregnated on to the solid porous material, the concentration of the transition metal on the solid porous material is such that it provides enhanced performance in the removal of nitrogen-containing contaminants from alcohol compositions compared to the solid porous material alone. Preferably, the concentration of the transition metal on the solid porous material may be in the range of from 0.1 to 50 wt %, more preferably from 0.2 to 30 wt %, even more preferably 0.3 to 25 wt %, such as 0.5 to 20 wt %, based on the weight of transition metal loaded relative to the overall weight of the transition metal-loaded solid porous material. Methods of impregnating transition metals on to the solid porous materials are known in the art.

If the transition metal is impregnated on to the solid porous material, it is preferred that the molar loading of transition metal relative to the concentration of cation-exchangeable sites on the solid porous material is at most 80 mol %, that is the molar amount of transition metal ions impregnation on the solid porous material should not be more than 80% of the molar amount of protons on the surface of the solid porous material based on the assumption that all cation-exchangeable site are protonated; more preferably the molar loading of transition metal relative to the concentration of cation-exchangeable sites on the solid porous material is in the range of from 1 to 50%, even more preferably from 2 to 40%, even more preferably from 3 to 30%, and most preferably from 5 to 25%, such as from 10 to 20%.

In one particular embodiment of the present invention, the adsorbent used is a transition metal-loaded zeolite. In one particular embodiment, the zeolite has at least one channel defined by a 10-membered or 12-membered ring, and preferably the zeolite has at least one channel defined by a 12-membered ring.

The zeolite is preferably a large-pore zeolite having at least one channel having a diameter of at least 5 Å, preferably at least one channel having a diameter of at least 6 Å, and most preferably at least one channel having a diameter of at least 7 Å.

In one embodiment, the zeolite has the framework type FAU or MOR, and is preferably a faujasite or a mordenite zeolite. In a specific aspect of this embodiment, the zeolite has the framework type FAU, and is preferably a faujasite; examples of faujasites are zeolite Y and zeolite X, with zeolite Y being identified as a particularly suitable zeolite.

As used herein, the term "transition metal-loaded zeolite" refers to any zeolite having a transition metal supported thereon. For instance, the copper-loaded zeolite may be obtained by ion-exchange of the cation-exchangeable sites of the zeolite, or by impregnation of a zeolite with a solution of transition metal salts. Suitable techniques are well-known in the art.

The zeolite prior to being loaded with the transition metal is preferably in the acidic (H) form, namely substantially all of the cation-exchangeable sites are occupied with a proton. Thus, preferred zeolites for loading with the transition metal include H-faujasites and H-mordenites, more preferably the zeolite is zeolite H—Y or zeolite H—X, such as zeolite H—Y.

Alternatively, a zeolite which is not in the acid form may be loaded with the transition metal, and subsequent to the loading of the transition metal on to the zeolite, any cation-exchangeable site which are not occupied with a transition metal ion are preferably converted to acid sites.

The density of cation-exchangeable sites in zeolites is dependent on the silica to alumina ratio (SAR) of the zeolite. The lower the SAR value the greater the proportion of aluminium atoms and the greater the density of cation-exchangeable sites. Thus, in preferred embodiments, the zeolite has an SAR of at most 100, for example in the range of from 1 to 100, more preferably has an SAR of at most 50, for example in the range of from 1 to 50, more preferably has an SAR of at most 20, for example in the range of from 1 to 20, still more preferably has an SAR of at most 15, for example in the range of from 1 to 15, and most preferably has an SAR of at most 10, for example in the range of from 1 to 10.

A particularly preferred zeolite adsorbent is zeolite H—Y having an SAR value in the range of from 2 to 10, for instance 4 to 8.

In one particular embodiment of the present invention, the adsorbent is a copper-loaded zeolite. Where the copper-loaded zeolite is prepared by ion-exchange, it is preferred that up to 80% of the cation-exchangeable sites of the zeolite are exchanged with $Cu^{2+}$ or $Cu^+$ ions, preferably $Cu^{2+}$ ions. More preferably, from 1 to 50% of the cation-exchangeable sites, still more preferably from 2 to 40% of the cation-exchangeable sites, even more preferably from 3 to 30% of the cation-exchangeable sites, and most preferably from 5 to 25% of the cation-exchangeable sites, such as from 10 to 20% of the cation-exchangeable sites of the zeolite are exchanged with $Cu^{2+}$ or $Cu^+$ ions. Preferably, the remaining cation-exchangeable sites of the zeolite are in the acidic form, thus it is most preferred to start the ion-exchange procedure from a zeolite in the acidic form. Alternatively, a zeolite in the ammonium form may be used for the ion-exchange procedure followed by conversion of the ammonium sites to acid sites by known procedures, for instance by calcining the ion-exchanged zeolite; likewise, other non-protonated forms of zeolites may be used for the ion-exchange procedure, wherein the non-protonated and non-transition-metal exchanged sites of the zeolite are converted to acid sites by known procedures, for instance by calcining the ion-exchanged zeolite.

Ion-exchange of zeolites is well-known in the art and typically involves contacting the zeolite with an aqueous solution of a metal salt under conditions effective to exchange at least a portion of the cation-exchangeable sites on the zeolite. In accordance with the present invention, suitable $Cu^+$ salts include copper(I) halides, such as CuCl, and copper(I) acetate (CuOAc). Suitable $Cu^{2+}$ salts include copper(II) halides, such as $CuCl_2$, copper(II) nitrate [$Cu(NO_3)_2$], copper(II) acetate [$Cu(OAc)_2$], copper(II) sulphate ($CuSO_4$), and copper(II) carbonate ($CuCO_3$).

As an alternative to ion-exchange, the zeolite may be impregnated with an aqueous solution of a copper salt, such as the copper salts described above, and subsequently dried. If the ammonium form or other non-acidic form of the zeolite is used, it is preferred to convert the cation-exchangeable sites of the zeolite to acid sites after the drying step, for instance by calcining the impregnated and dried zeolite.

Where the copper-loaded zeolite is prepared by impregnation it is preferred that the concentration of the copper on the solid porous material is in the range of from 0.1 to 50 wt %, more preferably from 0.2 to 30 wt %, even more preferably 0.3 to 25 wt %, such as 0.5 to 20 wt %, based on the weight of copper loaded relative to the overall weight of the copper-loaded zeolite.

Alternatively, where the copper-loaded zeolite is prepared by impregnation it is preferred that the molar loading of copper relative to the concentration of cation-exchangeable sites on the zeolite is in the range of from 1 to 50%, even more preferably from 2 to 40%, even more preferably from 3 to 30%, and most preferably from 5 to 25%, such as from 10 to 20%.

The temperature at which the alcohol composition contacts the adsorbent is preferably at least 0° C., more preferably at least 25° C., even more preferably at least 50° C., such as at least 75° C. or at least 100° C. Preferably, the temperature at which the alcohol composition contacts the adsorbent is at most 300° C., more preferably at most 275° C., even more preferably at most 250° C., such as at most 225° C. or at most 200° C.; lower maximum temperatures may be employed such as the use of a maximum temperature of at most 175° C. or at most 150° C. Preferred temperature ranges for contacting the alcohol composition with the adsorbent may be selected from the combinations of the above identified preferred minimum temperatures with the above identified maximum temperatures. Examples of suitable temperature ranges at which the alcohol composition may contact the adsorbent include temperature ranges of from 0° C. to 300° C., from 25° C. to 300° C., from 50° C. to 300° C., from 75° C. to 300° C., from 100° C. to 300° C., 0° C. to 275° C., from 25° C. to 275° C., from 50° C. to 275° C., from 75° C. to 275° C., from 100° C. to 275° C., 0° C. to 250° C., from 25° C. to 250° C., from 50° C. to 250° C., from 75° C. to 250° C., from 100° C. to 250° C., 0° C. to 225° C., from 25° C. to 225° C., from 50° C. to 225° C., from 75° C. to 225° C., from 100° C. to 225° C., 0° C. to 200° C., from 25° C. to 200° C., from 50° C. to 200° C., from 75° C. to 200° C., from 100° C. to 200° C., 0° C. to 175° C., from 25° C. to 175° C., from 50° C. to 175° C., from 75° C. to 175° C., from 100° C. to 175° C., 0° C. to 150° C., from 25° C. to 150° C., from 50° C. to 150° C., from 75° C. to 150° C., from 100° C. to 150° C. It has been found that while the removal of nitrogen-containing contaminants is effective throughout these temperatures ranges, some adsorbents may catalyse dehydration of the alcohols at higher temperatures. If it is desired to avoid any dehydration of the alcohol composition, appropriate temperatures may readily be selected to minimize any unwanted dehydration of the alcohol.

Due to the enhanced removal of nitrogen-containing contaminants which has been observed in the vapour phase, in one particular embodiment, the alcohol composition is contacted with the adsorbent at a temperature which is at least 5° C., preferably at least 10° C., above the dew point temperature of the alcohol composition at the operating pressure of the adsorption zone.

In the embodiment where the alcohol composition is in the vapour phase when it is contacted with the adsorbent in the adsorption zone, The pressure is selected such that the alcohol composition is in the vapour phase as it is brought into contact with the adsorbent. The skilled person is readily capable of selecting suitable operating pressures depending on the alcohol composition. In general, however, the pressure at which the alcohol composition contacts the adsorbent is preferably at least 0.1 bara (bar absolute), more preferably at least 0.25 bara, even more preferably at least 0.5 bara, even more preferably at least 0.75 bara and most preferably at least 1.0 bara (i.e. ambient pressure). Preferably, the pressure at which the alcohol composition contacts the adsorbent is at most 25 bara, more preferably at most 20 bara, even more preferably at most 15 bara, lower maximum pressures may be beneficially employed such as the use of a maximum pressure of at most 10 bara or even 5 bara. Preferred pressure ranges for contacting the alcohol composition with the adsorbent may be selected from the combinations of the above identified preferred minimum pressures with the above identified maximum pressures. Examples of suitable pressure ranges at which the alcohol composition may contact the adsorbent include pressure ranges of from 0.1 to 25 bara, from 0.25 to 25 bara, from 0.5 to 25 bara, from 0.75 to 25 bara, from 1.0 to 25 bara, 0.1 to 20 bara, from 0.25 to 20 bara, from 0.5 to 20 bara, from 0.75 to 20 bara, from 1.0 to 20 bara, 0.1 to 15 bara, from 0.25 to 15 bara, from 0.5 to 15 bara, from 0.75 to 15 bara, from 1.0 to 15 bara, 0.1 to 10 bara, from 0.25 to 10 bara, from 0.5 to 10 bara, from 0.75 to 10 bara, from 1.0 to 10 bara, 0.1 to 5 bara, from 0.25 to 5 bara, from 0.5 to 5 bara, from 0.75 to 5 bara, from 1.0 to 5 bara. In one particular embodiment where the alcohol composition is in the vapour phase when it is contacted with the adsorbent in the adsorption zone, the alcohol composition is contacted with the adsorbent at a pressure which is at least 0.1 bar, preferably at least 0.2 bar, below the dew point pressure of the alcohol composition at the operating temperature of the adsorption zone.

As used herein, the dew point temperature of the alcohol composition is the temperature, at a given pressure, at which the alcohol component(s) of the vapour-phase alcohol composition will start to condense out of the gaseous phase. Likewise, as used herein, the dew point pressure of the alcohol composition is the pressure, at a given temperature, at which the alcohol component(s) of the vapour-phase alcohol composition will start to condense out of the gaseous phase.

The alcohol composition is preferably contacted with the adsorbent at a liquid hourly space velocity relative to the volume of adsorbent of from 0.01 to 100 $h^{-1}$, more preferably from 0.1 to 10 $h^{-1}$, and most preferably from 0.5 to 2 $h^{-1}$, based on the volume of alcohol composition at 25° C. and 1 bar. It will be appreciated that although the flow rate is defined herein in terms of a liquid hourly space velocity, the alcohol composition may be in the vapour phase when it is contacted with the adsorbent.

The processes of the present invention may be operated as continuous or batch process, preferably as continuous processes. Preferably, the processes of the invention are carried out by passing the alcohol composition in the vapour phase through a fixed bed, fluidised bed or moving bed of the adsorbent. Multiple adsorption zones may also be used in the process of the present invention, wherein each adsorption zone may contain the same or different adsorbents and may be operated at the same or different conditions. One particular example of the use of multiple adsorption zones comprises treating the alcohol in a system comprising at least two adsorption zones, wherein at least one adsorption zone is operating under conditions such that the alcohol composition is contacted with an adsorbent in the liquid phase and at least one adsorption zone is operating under conditions such that the alcohol composition is contacted with an adsorbent in the vapour phase.

The alcohol composition may optionally be contacted with the adsorbent in the presence of an inert carrier gas. Examples of suitable inert carrier gases include nitrogen ($N_2$) and argon.

In the case where there alcohol composition comprises a dehydratable alcohol, the process for treating an alcohol composition according to the first aspect of the present invention may be integrated with a process for the dehydration of alcohols to form olefins. Therefore, according to a second aspect of the present invention there is provided a process for the preparation of olefins from an alcohol composition comprising a dehydratable alcohol and nitrogen-containing contaminants, the process comprising:

(i) contacting the alcohol composition with an adsorbent in an adsorption zone, wherein the adsorbent is a transition metal-loaded solid porous material selected from the group consisting of aluminosilicates, silica-aluminas, silicates and aluminas, to form a treated alcohol composition; and (ii) contacting the treated alcohol composition with an alcohol dehydration catalyst in an alcohol dehydration zone under conditions effective to dehydrate the alcohol to the corresponding olefin.

As step (i) of the second aspect of the present invention corresponds to the first aspect of the present invention, all of the preferences and embodiments expressed in relation to the first aspect of the present invention are equally applicable in the second aspect of the present invention.

If the treated alcohol composition from step (i) is in the vapour phase, it may be fully or partially condensed prior to feeding to the alcohol dehydration zone in step (ii) of the process of the second aspect of the invention. However, since alcohol dehydration processes are typically performed in the vapour phase, if the treated alcohol composition from step (i) is in the vapour phase, it may conveniently pass from the adsorption zone of step (i) to the alcohol dehydration zone of step (ii) with the alcohol remaining in the vapour phase.

Preferably, in step (ii) of the process according to the second aspect of the invention, the treated alcohol composition is contacted with the alcohol dehydration catalyst in the vapour phase. Thus, in the embodiment where step (i) of the process of the second aspect of the present invention is performed in the vapour phase, vaporisation of the alcohol for the removal of nitrogen-containing contaminants may be integrated with vapour phase alcohol dehydration. In such an embodiment, the temperature and pressure of the alcohol dehydration step (ii) may be greater than the temperature and pressure of the treated alcohol composition resulting from step (i) of the process according to the second aspect of the invention, thus the temperature and pressure of the treated alcohol composition may need to be adjusted prior to contacting the treated alcohol composition with the alcohol dehydration catalyst; alternatively, the temperature and pressure of the alcohol treatment step (i) in the second aspect of the present invention may be selected such that the treated alcohol composition resultant from the adsorption zone is at the same temperature and pressure as the alcohol dehydration zone.

The alcohol dehydration catalyst may be any of the alcohol dehydration catalysts that are known in the art. For example, the alcohol dehydration catalyst may be a crystalline silicate, a dealuminated crystalline silicate or a phosphorus modified zeolite as described in WO 2009/098262, the contents of which are incorporated herein by reference. Alternatively, the alcohol dehydration catalyst may be a heteropolyacid catalyst, for instance as described by WO 2008/138775 and WO 2008/062157, the contents of which are incorporated herein by reference. In preferred embodiments, the alcohol dehydration catalyst is a heteropolyacid catalyst. The heteropolyacid catalyst is preferably supported on a suitable inert support, such as silica or alumina.

Suitable conditions for dehydrating alcohols are well-known in the art and to the skilled person, for instance with reference to the prior art documents cited herein. However, in the case of a crystalline silicate or zeolite alcohol dehydration catalyst, typical reaction conditions include a temperature of from 280 to 500° C., a total pressure of from 0.5 to 30 bara, and a partial pressure of alcohol that is preferably from 1.2 to 4 bara. In the case of a heteropolyacid catalyst, typical reaction conditions include a temperature of from 180 to 270° C. and a pressure of from 1 to 45 bara.

An olefin product may be recovered from the alcohol dehydration zone and may subsequently be used in a wide range of industrial applications, for instance in the preparation of polymers and oligomers, as components of fuels and lubricants and in the preparation of surfactants.

In further embodiments, the present invention provides a polymeric product obtained by polymerisation of olefins produced according to the second aspect of the invention, an oligomeric product obtained by oligomerisation of olefins produced according to the second aspect of the invention, fuel and lubricant compositions comprising said olefins and/or said oligomeric or polymeric products, and surfactant compositions comprising said olefins and/or said oligomeric or polymeric products.

BRIEF DESCRIPTION OF THE DRAWINGS

The present invention will now be illustrated, without limiting the scope thereof, with reference to the following Examples and the accompanying Figures, in which.

EXAMPLES

In the following Examples, the removal of nitrogen containing contaminants using zeolite adsorbents was examined in the liquid and vapour phases.

Apparatus

Liquid phase experiments were carried out using a Vapourtec™ reactor unit. The apparatus comprises a feed reservoir, and HPLC pump, a pre-heater, a reactor tube, a cool-down section and a product reservoir. In each experiment the reactor tube was loaded with 20 mL of adsorbent. The adsorbent bed was flushed with ~150 mL of pure synthetic ethanol using flow rates up to 7.5 mL/min. This process removed trapped airbubbles from the adsorbent bed thus preventing channelling. Reactions were all carried out with a LHSV of 1 relative to the volume of adsorbent (0.333 mL/min). The process was carried out over four consecutive days and stopped overnight (~24 hours total run time). The first day of each new experiment used a pure synthetic ethanol feed to ensure a reliable baseline. Bio-ethanol was fed on the subsequent 3 days. When restarting the process each day, the resin bed was washed with ~40 mL of the bio-ethanol feed prior to sample collection to avoid results being distorted by possible leaching of nitrogen-containing contaminants from the adsorbent bed into the stationary liquid alcohol phase overnight. Samples collected on each of the four consecutive days were analysed by chemiluminescence, ion-chromatography, GC and GC-NPD techniques.

Figure 1:
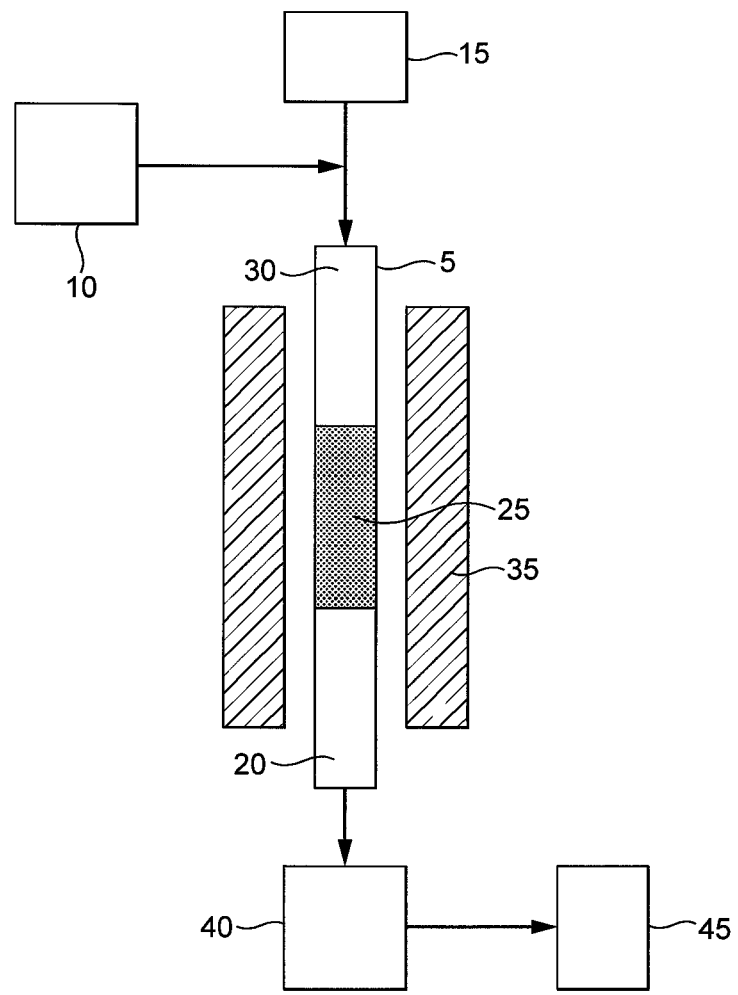
FIG. 1 shows a schematic of an experimental apparatus for testing the removal of nitrogen compounds from alcohol compositions in the vapour phase.

The experimental set-up for vapour phase reactions is shown in FIG. 1. The apparatus comprises a quartz reactor tube (5) fitted with a porosity 1 quartz frit (not shown) and connected to a syringe pump (10) to supply the alcohol composition and to a source of nitrogen carrier gas (15). The reactor tube was loaded with 12 mL carborundum (20), 5 mL of the active zeolite material (25) and a further 12 mL of carborundum (30) to act as a vaporiser. In order to ensure effective gas flow through the zeolite bed all zeolites were pressed (12 tonnes, 32 mm die set) and sieved (250-500 µm) prior to use. The reactor tube was secured in a Carbolite™ tube furnace (35) and heated to the desired temperature. A cooled liquid trap (40) was provided to collect the treated alcohol and a gas collection vessel (45) was supplied to collect non-condensable components.

In each vapour phase experiment, the $N_2$ flow rate was 50 mL/min and the liquid flow rate was 5 mL/hour (LHSV=1). Vapour phase reactions were conducted at ambient pressure unless stated otherwise. Liquid and gaseous samples were analysed by GC and GC-NPD.

Alcohol Compositions

In the following Examples, the clean up of a bioethanol composition is examined; the bioethanol composition having a total nitrogen content of approximately 6.1 ppmw. Details of the amounts of contaminants present in the bioethanol composition are provided in Table 1.

TABLE 1

| Contaminant | Amount |
| --- | --- |
| Other alcohols | 425 mg/kg |
| Non-alchol oxygenates | 1245 mg/kg |
| Water | 0.15 wt % |
| Total nitrogen | 6.1 ppmw |
| Nitrogen as acetonitrile | 240 ppbw |
| Total acetonitrile | 700 ppbw |

Figure 2:
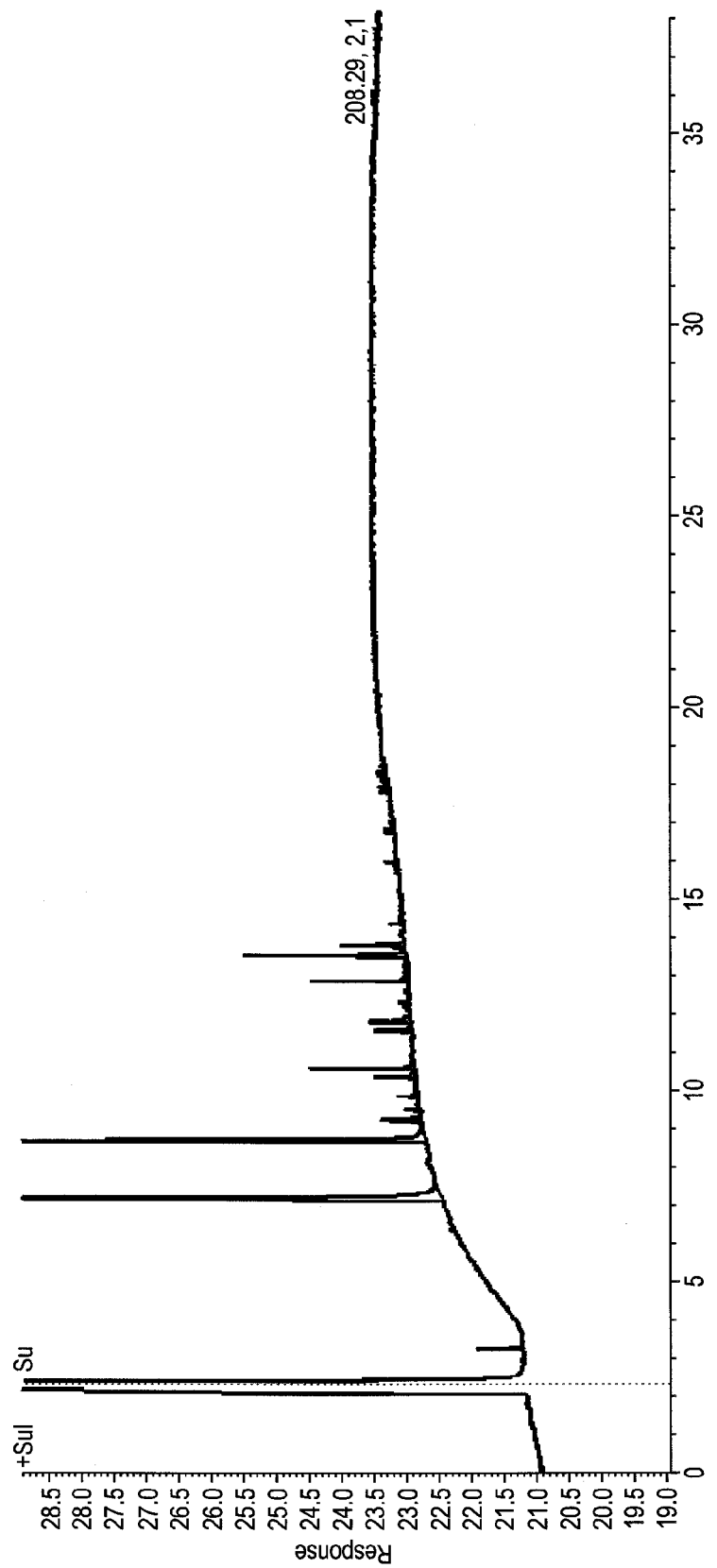
FIG. 2 shows a GC-NPD chromatogram for the bioethanol composition prior to treatment for the removal of nitrogen containing compounds.

The GC-NPD chromatogram for the bioethanol composition prior to treatment to remove nitrogen-containing contaminants is shown in FIG. 2. The peak at ca. 2.4 min is bioethanol, and the remaining peaks are nitrogen-containing contaminants.

Example 1

Preparation of Ion-Exchanged Cu—HY Zeolite

HY zeolite (SAR 5.2) (100 g) was added to a 2 L Erlenmeyer flask with deionised water (500 mL) and stirred for 5 minutes. A solution of copper acetate hydrate (30 g, 150 mmol) in deionised water (200 mL) was added to the zeolite mixture and the resulting mixture was heated to 80° C. for 3 hours. The mixture was filtered through a sintered funnel and the resulting solid was returned to the Erlenmeyer flask and was stirred with deionised water (500 mL). This step was then repeated. The mixture was filtered once again and the resulting solid was dried overnight at 110° C. The dried solid was then calcined at 400° C. for 5 hours to remove all volatile materials. Analysis showed that the zeolite contained 4 wt % copper and 10.1 wt % aluminium, equating to a copper loading of 17 mol % relative to aluminium.

Example 2

Preparation of Ion-Exchanged Cu-HMOR Zeolite $NH_4$-mordenite (SAR 20) (100 g) was added to a 2 L Erlenmeyer flask with a solution of copper(II) nitrate (7.42 g) in deionised water (1 L) and stirred for 2 hours at 80° C. The mixture was filtered through a sintered funnel and the resulting solid was returned to the Erlenmeyer flask and was stirred with deionised water (500 mL). This step was then repeated. The mixture was filtered once again and the resulting solid was dried overnight at 110° C. The dried solid was then calcined at 500° C. for 5 hours to remove all volatile materials. ICP spectroscopic analysis showed that the zeolite contained 1.1 wt % copper and 3.3 wt % aluminium, equating to a copper loading of 14 mol % relative to aluminium.

Comparative Example A

Vapour Phase Testing with Zeolite HY

Figure 3A:
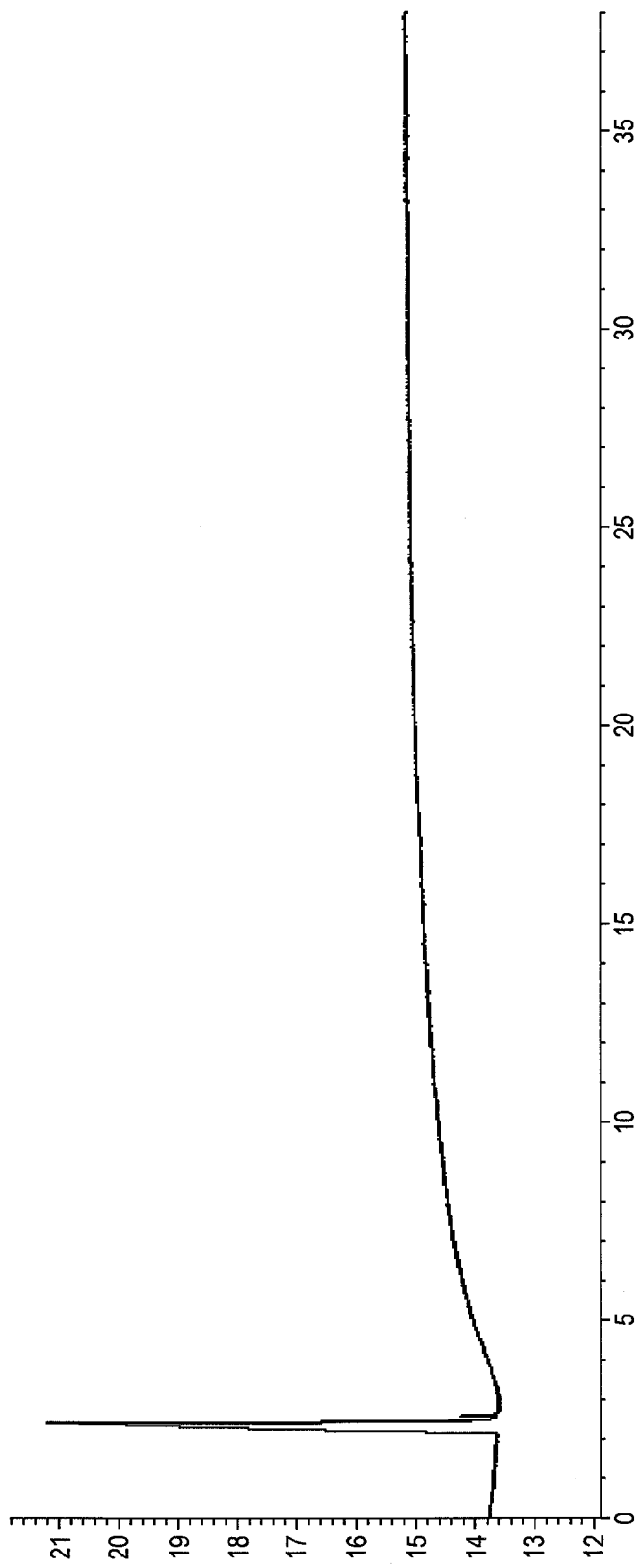
FIG. 3a shows a GC-NPD chromatogram for the bioethanol composition following contacting with zeolite HY (SAR=5.2) at 150° C. in the vapour phase.
Figure 3B:
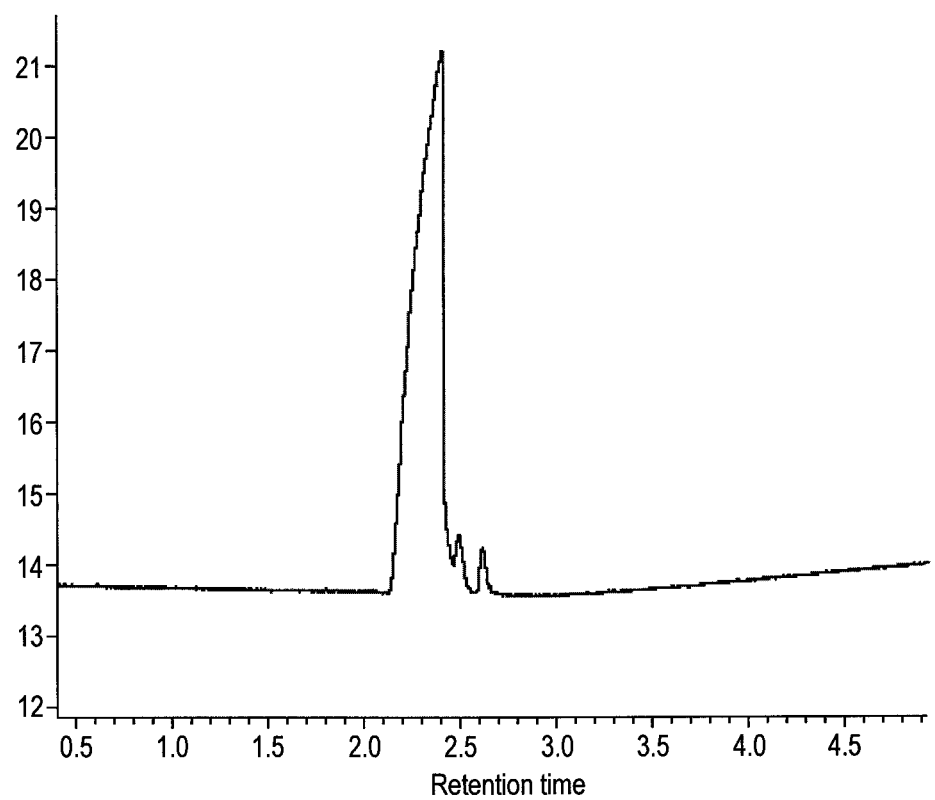
FIG. 3b shows in enlargement the portion of the GC-NPD chromatogram of FIG. 3a between ca. 0.5 and 4.5 minutes.

In this Example, the removal of nitrogen-containing contaminants from the bioethanol composition was examined in the vapour phase using zeolite HY (SAR=5.2) as the adsorbent at 150° C. and at ambient pressure. The GC-NPD chromatogram for this test is shown in FIG. 3a with an enlargement of the portion of the GC-NPD chromatogram between ca. 0.5 and 4.5 minutes in FIG. 3b.

The GC-NPD chromatogram shows that, while nitrogen-containing contaminants were almost completely removed at 150° C., however, complete removal of acetonitrile was not obtained (approximately 290 ppbw acetonitrile remained).

Example 3

Vapour Phase Testing with Zeolite Cu—HY

Figure 4A:
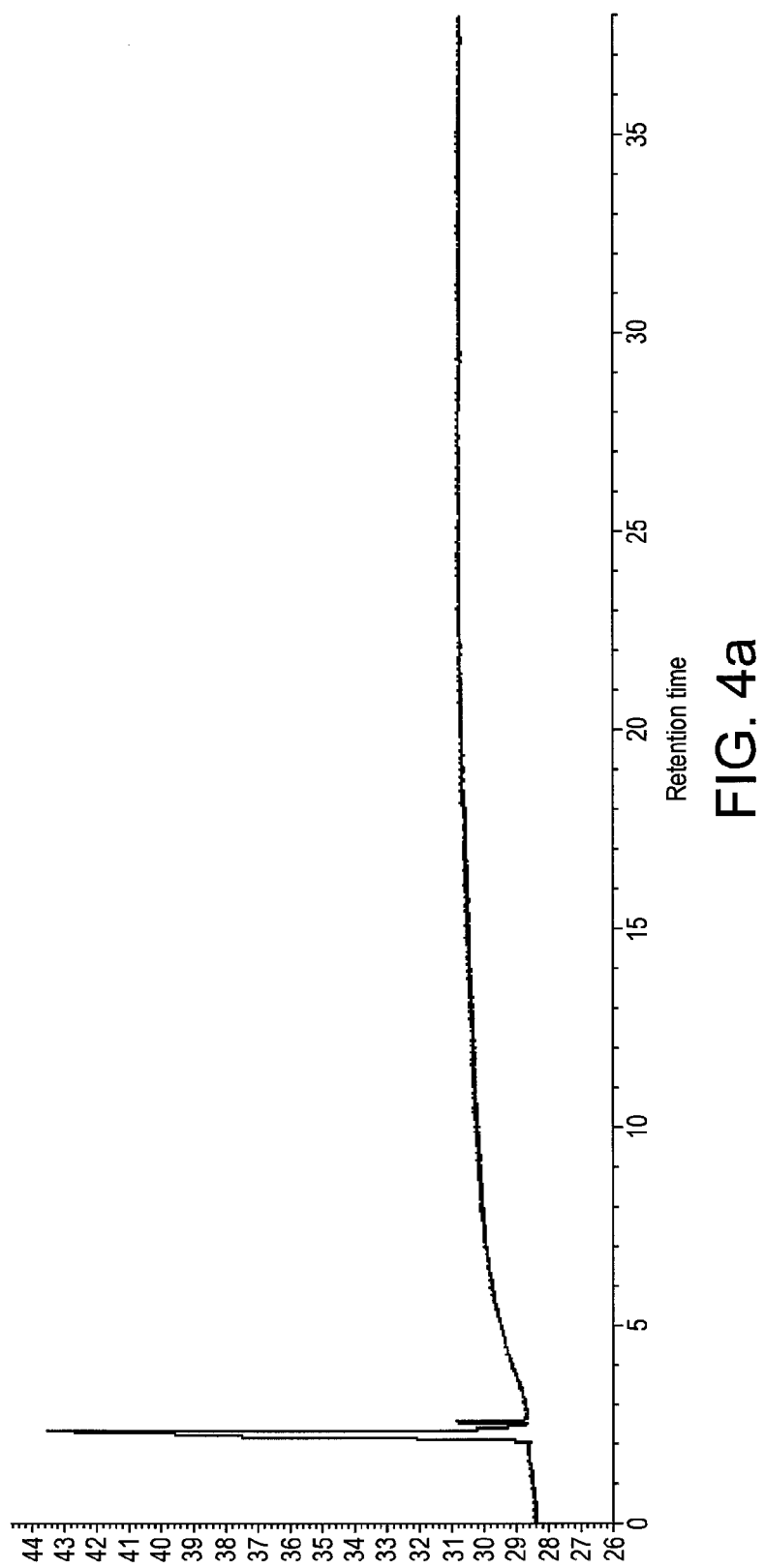
FIG. 4a shows a GC-NPD chromatogram for the bioethanol composition following contacting with zeolite Cu—HY (SAR=5.2) at 150° C. in the vapour phase.
Figure 4B:
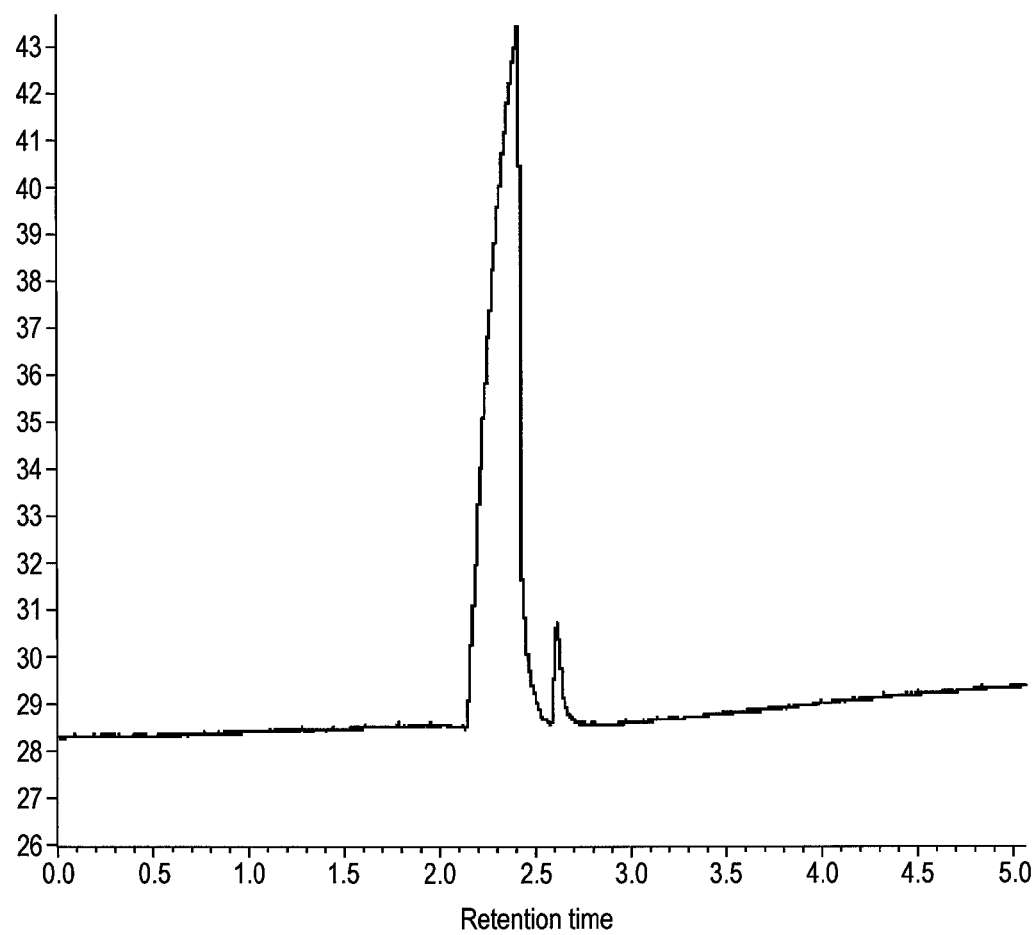
FIG. 4b shows in enlargement the portion of the GC-NPD chromatogram of FIG. 4a between ca. 0.5 and 4.5 minutes.

In this Example, the removal of nitrogen-containing contaminants from the bioethanol composition was was examined in the vapour phase using the zeolite of Example 1 as the adsorbent at 150° C. and at ambient pressure. The GC-NPD chromatograms for this test is shown in FIG. 4a with an enlargement of the portion of the GC-NPD chromatogram between ca. 0.5 and 4.5 minutes in FIG. 4b.

The GC-NPD chromatogram shows that nitrogen-containing contaminants, including acetonitrile, were completely removed to below the limits of detection of GC-NPD.

Examples 4 and 5

Liquid Phase Testing

Figure 5:
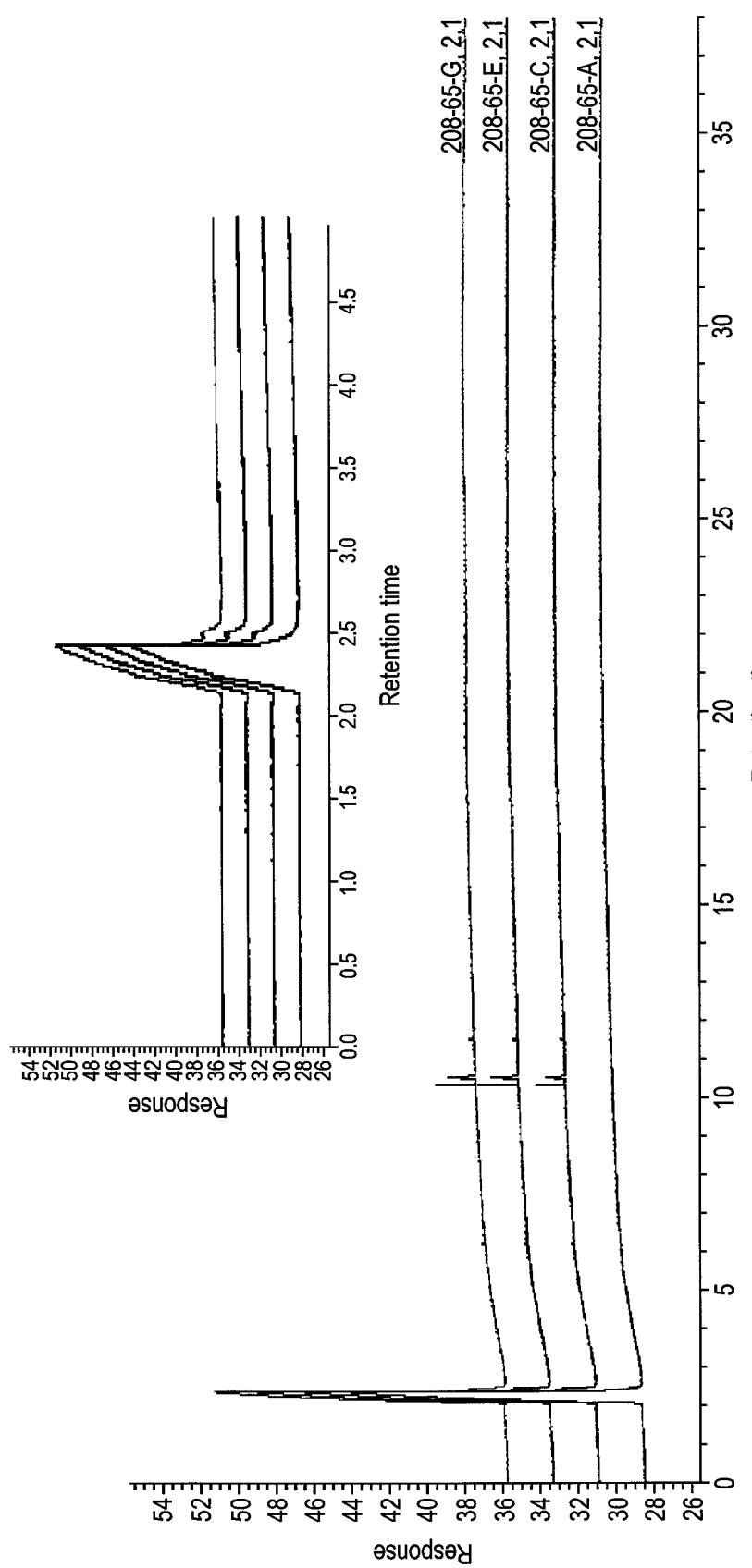
FIG. 5 shows a GC-NPD chromatogram for the bioethanol composition following contacting with zeolite Cu—HY (SAR=5.2) at 25° C. in the liquid phase.
Figure 6:
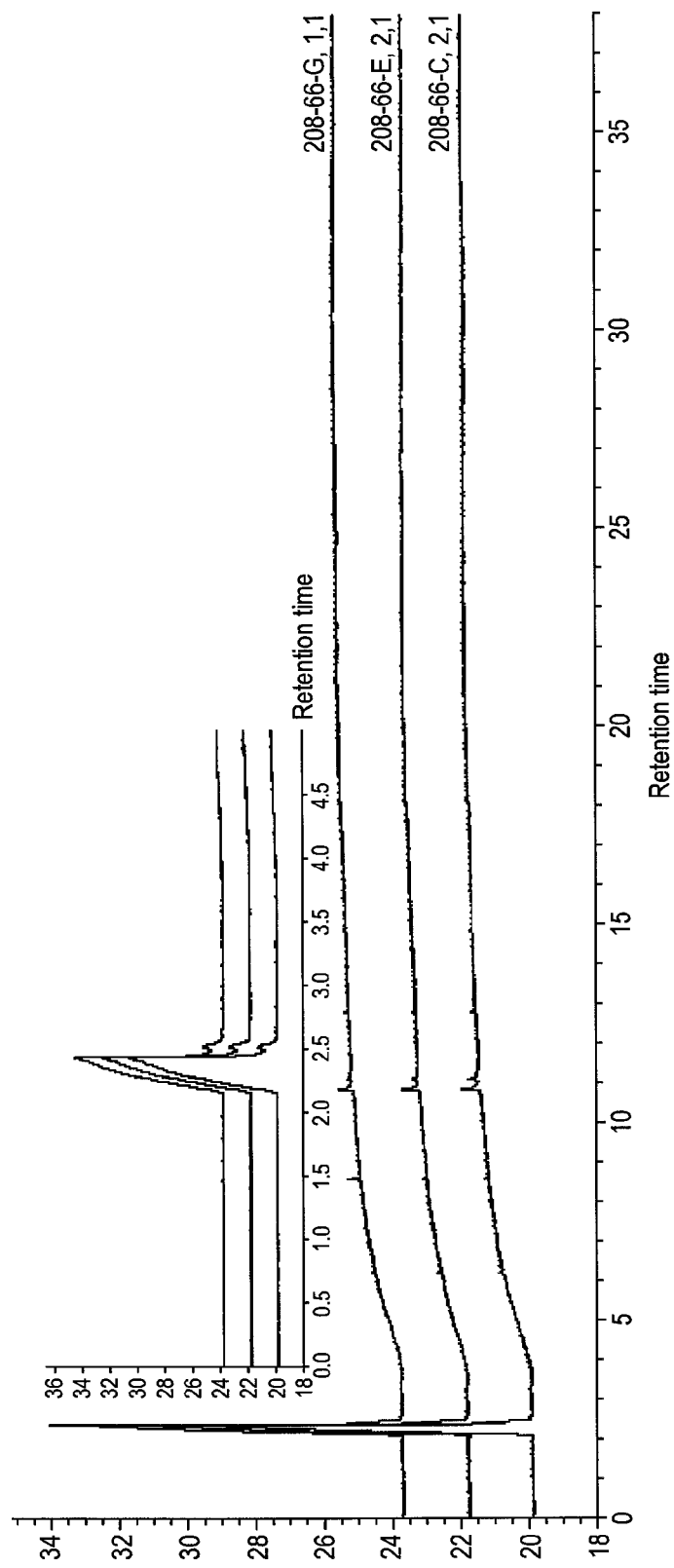
FIG. 6 shows a GC-NPD chromatogram for the bioethanol composition following contacting with zeolite Cu—H-Mordenite (SAR=5.2) at 130° C. in the liquid phase.

In these Examples, the removal of nitrogen-containing contaminants from the bioethanol composition was examined in the liquid phase using zeolite Cu—HY (SAR=5.2) of Example 1 as the adsorbent at 25° C. (Example 4) and at 130° C. (Example 5). The GC-NPD chromatographs for Examples 4 and 5 are shown in FIGS. 5 and 6 respectively; inset into each of FIGS. 5 and 6 is an enlargement of the section of the chromatographs between ca. 0 and 5 minutes.

Comparative Example B

Vapour Phase Testing with Zeolite HMOR

Figure 7:
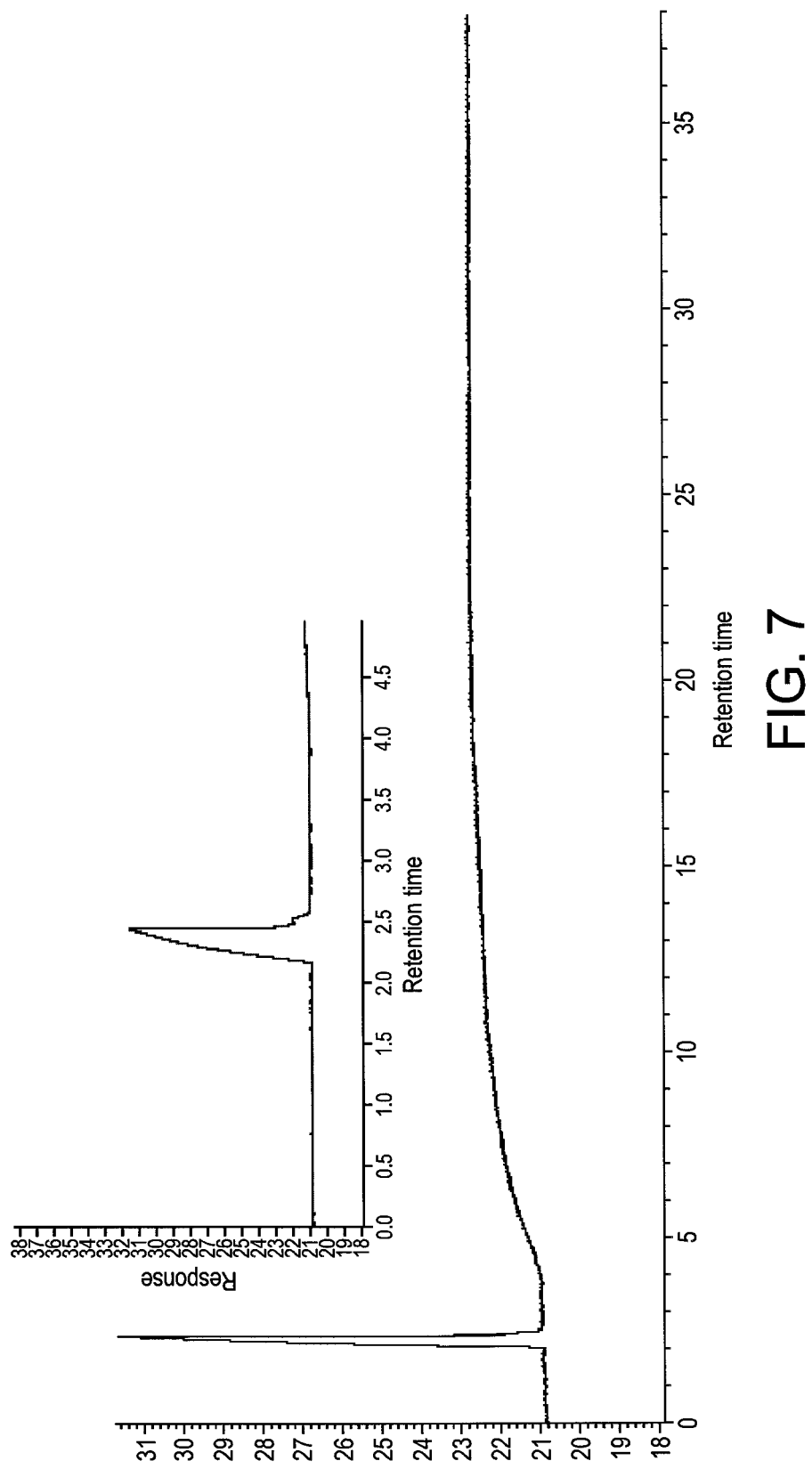
FIG. 7 shows a GC-NPD chromatogram for the bioethanol composition following contacting with zeolite H-Mordenite (SAR=20) at 150° C. in the vapour phase.

In this Example, the removal of nitrogen-containing contaminants from the bioethanol composition was examined in the vapour phase using zeolite HMOR (SAR=20) as the adsorbent at 150° C. and at ambient pressure. The GC-NPD chromatograms for this test is shown in FIG. 7. The portion of the chromatogram between ca. 0.5 and 4.5 minutes is shown inset in enlargement.

The GC-NPD chromatogram shows that while nitrogen-containing contaminants were almost completely removed at 150° C., however, complete removal of acetonitrile was not obtained (approximately 250 ppbw acetonitrile remained).

Example 6

Vapour Phase Testing with Zeolite Cu-HMOR

Figure 8:
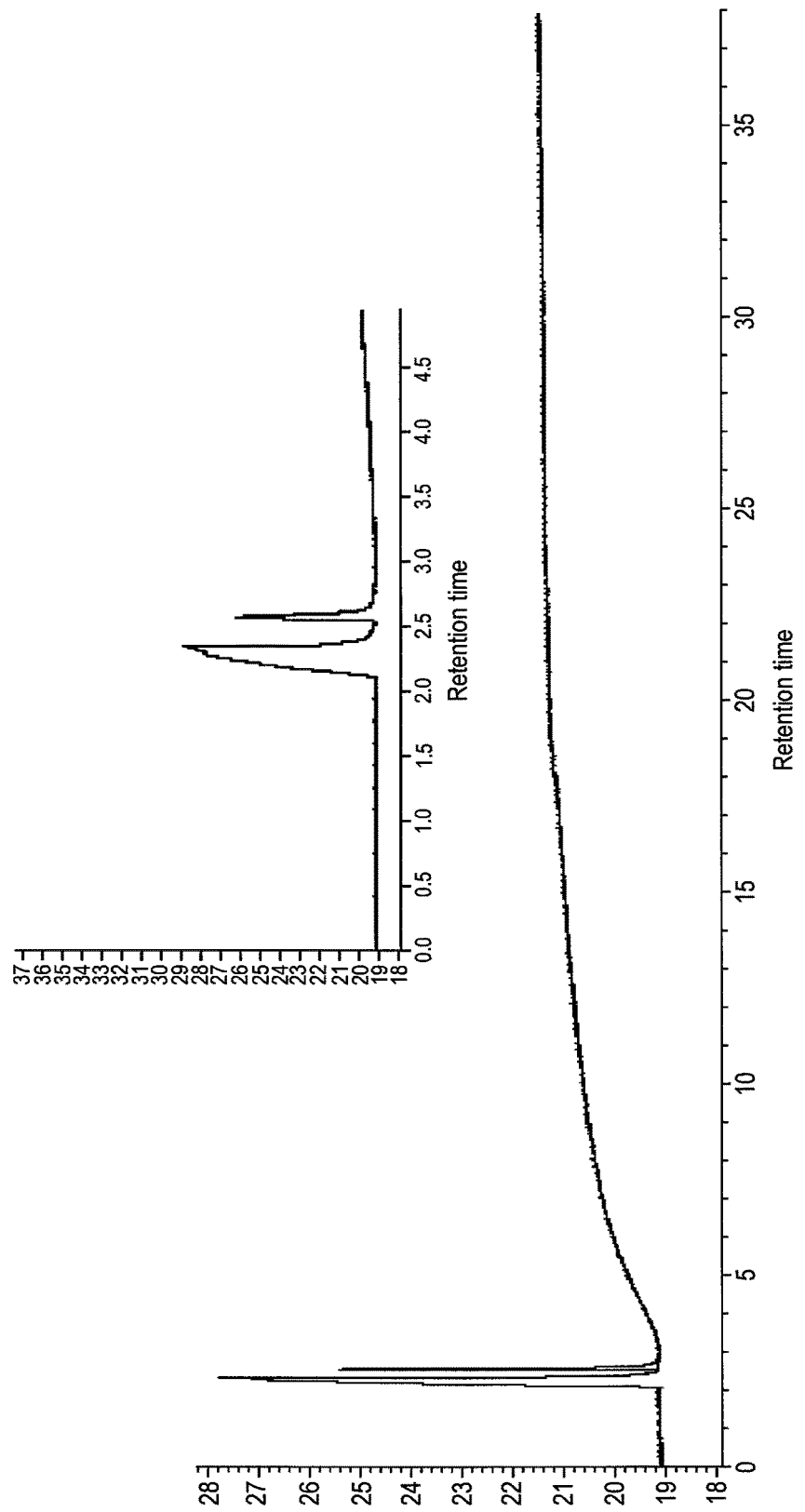
FIG. 8 shows a GC-NPD chromatogram for the bioethanol composition following contacting with zeolite Cu—H-Mordenite (SAR=20) at 150° C. in the vapour phase.

In this Example, the removal of nitrogen-containing contaminants from the bioethanol composition was examined in the vapour phase using zeolite Cu-HMOR (SAR=5.2) of Example 2 as the adsorbent at 150° C. and at ambient pressure. The GC-NPD chromatograms for this test is shown in FIG. 8. The portion of the chromatogram between ca. 0.5 and 4.5 minutes is shown inset in enlargement.

The GC-NPD chromatogram shows that nitrogen-containing contaminants, including acetonitrile, were completely removed to below the limits of detection of GC-NPD.

The GC-NPD chromatogram includes a peak at ca. 2.65 minutes retention time, demonstrating that diethyl ether is formed.

The invention claimed is:

1. A process for the treatment of an alcohol composition comprising nitrogen-containing contaminants, the process comprising contacting the alcohol composition with an adsorbent in an adsorption zone, wherein the adsorbent is a transition metal-loaded solid porous material selected from the group consisting of aluminosilicates, silica-aluminas, silicates and aluminas, and wherein the alcohol composition is contacted with the adsorbent either alone or in the presence of an inert carrier gas.

2. A process according to claim 1, wherein the alcohol composition comprises one or more alcohols produced from a biological source.

3. A process according to claim 2, wherein the alcohol composition comprises bio-ethanol.

4. A process according to claim 1, wherein the nitrogen-containing contaminants comprise one or more nitrogen-containing compounds from the group consisting of nitriles, amines, ammonium cations, amides, imides and mixtures thereof.

5. A process according to claim 4, wherein the alcohol composition comprises one or more nitriles.

6. A process according to claim 5, wherein the alcohol composition comprising nitrogen-containing contaminants is an ethanol-containing composition that comprises acetonitrile.

7. A process according to claim 5, wherein the alcohol composition comprises at least 0.025 ppmw nitrogen in the form of nitriles.

8. A process according claim 1, wherein the solid porous material of the adsorbent is selected from the group consisting of aluminosilicates and silica-aluminas.

9. A process according to claim 1, wherein the solid porous material of the adsorbent is a zeolite.

10. A process according to claim 9, wherein the zeolite has at least one channel defined by a 10-membered or 12-membered ring.

11. A process according to claim 10, wherein the zeolite is selected from zeolites having the framework types FAU or MOR.

12. A process according to claim 11, wherein the zeolite is zeolite Y or mordenite.

13. A process according to claim 1, wherein the transition metal in the transition metal-loaded zeolite is selected from zinc, copper, nickel, cobalt, iron, manganese, chromium and silver.

14. A process according to claim 13, wherein the transition metal is copper.

15. A process according to claims 9, wherein the transition metal-loaded zeolite is obtained by ion-exchange and wherein from 1 to 50% of the cation-exchangeable sites of the zeolite are exchanged with transition metal ions.

16. A process according to claim 15, wherein the remainder of the cation-exchangeable sites of the zeolite are in the acidic form.

17. A process according to claim 1, wherein the alcohol composition is in the vapour phase when it is contacted with the adsorbent in the adsorption zone.

18. A process according to claim 1, wherein the alcohol composition is contacted with the adsorbent in the adsorption zone at a temperature in the range of from 0° C. to 300° C., or from 25° C. to 275° C., or from 50° C. to 250° C., or from 75° C. to 225° C. or from 100° C. to 200° C.

19. A process according to claim 1, wherein the alcohol compositions is contacted with the adsorbent at a pressure of from 0.1 to 25 bara, or from 0.5 to 20 bara, or from 0.75 to 15 bara, or from 1 to 15 bara.

* * * * *